US009121756B2

(12) United States Patent
Wang et al.

(10) Patent No.: US 9,121,756 B2
(45) Date of Patent: Sep. 1, 2015

(54) METHOD AND SYSTEM FOR IMPROVING PRECISION OF ELEMENT MEASUREMENT BASED ON LASER-INDUCED BREAKDOWN SPECTROSCOPY

(75) Inventors: Zhe Wang, Beijing (CN); Zheng Li, Beijing (CN); Tingbi Yuan, Beijing (CN); Zongyu Hou, Beijing (CN); Lizhi Li, Beijing (CN); Jie Feng, Beijing (CN)

(73) Assignee: TSINGHUA UNIVERSITY, Beijing (CN)

( * ) Notice: Subject to any disclaimer, the term of this patent is extended or adjusted under 35 U.S.C. 154(b) by 0 days.

(21) Appl. No.: 14/000,356

(22) PCT Filed: Aug. 30, 2011

(86) PCT No.: PCT/CN2011/079129
§ 371 (c)(1),
(2), (4) Date: Oct. 16, 2013

(87) PCT Pub. No.: WO2012/109892
PCT Pub. Date: Aug. 23, 2012

(65) Prior Publication Data
US 2014/0036253 A1    Feb. 6, 2014

(30) Foreign Application Priority Data

Feb. 18, 2011   (CN) .......................... 2011 1 0040537
Jul. 26, 2011   (CN) .......................... 2011 1 0210361

(51) Int. Cl.
*G01N 1/00*       (2006.01)
*G01J 3/02*       (2006.01)
(Continued)

(52) U.S. Cl.
CPC ................ *G01J 3/0202* (2013.01); *G01J 3/44* (2013.01); *G01N 1/286* (2013.01); *G01N 21/718* (2013.01); *G01N 21/274* (2013.01)

(58) Field of Classification Search
CPC ........ G01N 21/718; G01N 21/274; G01J 3/44
USPC .......................................................... 356/36
See application file for complete search history.

(56) References Cited

U.S. PATENT DOCUMENTS

| 5,425,263 | A * | 6/1995 | Davies et al. ................ 73/28.05 |
| 7,113,277 | B2 | 9/2006 | Craig |
| 7,251,022 | B2 | 7/2007 | Martin et al. |
| 2003/0231306 | A1 | 12/2003 | Gornushkin et al. |

FOREIGN PATENT DOCUMENTS

| CN | 101655459 A | 2/2010 |
| CN | 101696936 A | 4/2010 |

(Continued)

OTHER PUBLICATIONS

International Search Report mailed Oct. 20, 2011 for PCT/CN2011/079129.

(Continued)

*Primary Examiner* — Roy M Punnoose
(74) *Attorney, Agent, or Firm* — Lowe Hauptman & Ham, LLP

(57) ABSTRACT

The present invention provides a method and a system for improving the precision of element measurement based on laser-induced breakdown spectroscopy. The method comprises: press-forming a sample to be measured with a tablet press; making a cavity on or immediately above a surface of the press formed sample; forming a layer of aerosol immediately above the surface of the sample to be measured with the components thereof completely identical to those of the sample to be measured; testing the sample to be measured by using a laser-induced breakdown spectroscopic system, so as to obtain the intensities of the characteristic spectral lines of a target element in the sample to be measured; and determining the concentration of the target element in the sample to be measured according to a calibration curve of the target element in prearranged calibration samples.

8 Claims, 5 Drawing Sheets

(51) Int. Cl.
  *G01N 21/71* (2006.01)
  *G01J 3/44* (2006.01)
  *G01N 1/28* (2006.01)
  *G01N 21/27* (2006.01)

(56) References Cited

FOREIGN PATENT DOCUMENTS

| | | |
|---|---|---|
| CN | 101915753 A | 12/2010 |
| KR | 20080114498 A | 12/2008 |
| KR | 20100055666 A | 5/2010 |
| WO | 02063284 A2 | 8/2002 |
| WO | 2007025113 A2 | 3/2007 |

OTHER PUBLICATIONS

Wang Jianwei, Zhang Nazhen, Hou Keyong, and Li Haiyang, Application of LIBS Technology to the Rapid Measure of Heavy Metal Contamination in Soils, Progress in Chemistry, Aug. 2008, pp. 1165-1171, vol. 20 No. 7/8, Dalian Institute of Chemical Physics, Chinese Academy of Sciences, Dalian, China.

J.A. Aguilera, C. Aragon, and J. Campos, Determination of Carbon Content in Steel Using Laser-Induced Breakdown Spectroscopy, Applie Spectroscopy, Apr. 20, 1992, pp. 1382-1387, vol. 46, No. 9, Catedra de Fisica Atomica, Facultad de Ciencias Fisicas, Universidad Complutense de Madrid, Madrid, Spain.

Chinese Office Action for application 201110040537.7 dated Feb. 29, 2012, citing the above reference(s).

Chinese Office Action for application 201110210361.5 dated Sep. 6, 2012, citing the above reference(s).

Chinese Notice of Allowance for application 201110040537.7 dated Oct. 23, 2012, citing the above reference(s).

Chinese Notice of Allowance for application 201110210361.5 dated Apr. 9, 2013, citing the above reference(s).

* cited by examiner

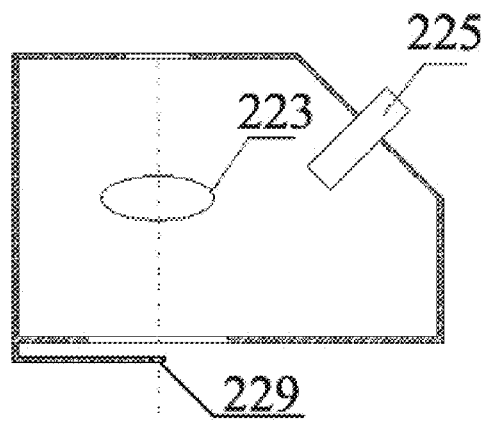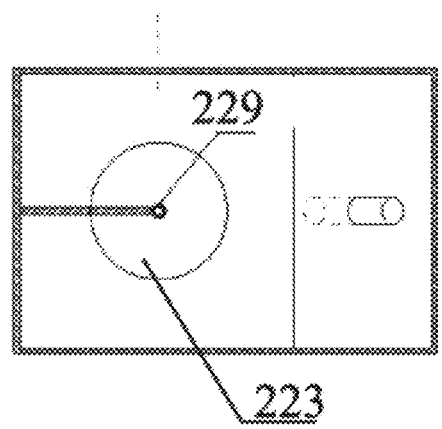
Fig 5(A)　　　　　　　　Fig 5(B)
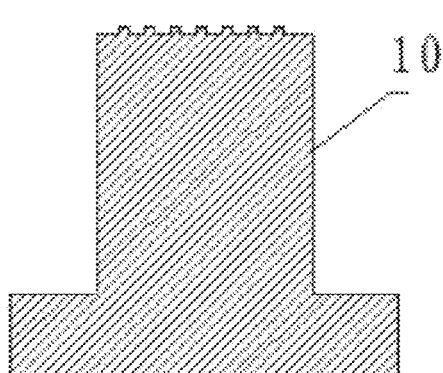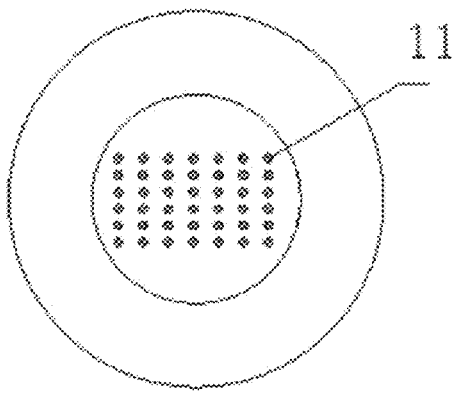
Fig 6(A)　　　　　　　　Fig 6(B)

METHOD AND SYSTEM FOR IMPROVING PRECISION OF ELEMENT MEASUREMENT BASED ON LASER-INDUCED BREAKDOWN SPECTROSCOPY

CROSS REFERENCE TO RELATED APPLICATION

This application claims the priority of Chinese Patent Application No. 201110040537.7, filed on Feb. 18, 2011 and No. 201110210361.5, filed on Jul. 26, 2011 in the Chinese Intellectual Property Office. Further, this application is the National Phase application of International Application No. PCT/CN2011/079129 filed on Aug. 30, 2011, which designates the United States and was published in Chinese.

TECHNICAL FIELD

The invention relates to the technical field of measurement by spectra emitted by atoms, and more particularly, to a method and a system for improving the precision of element measurement based on laser-induced breakdown spectroscopy.

BACKGROUND OF THE INVENTION

Laser-induced breakdown spectroscopy (LIBS) is a novel technology for analyzing physical elements which is developed in the late 20th century. The operating principle of LIBS is that: under the effect of a strong laser pulse, within a region of the surface of a sample on which the laser focuses, atoms, molecules and the like, which constitute the sample substance, are actuated into plasma after a series of processes including multiphoton ionization, absorption of photons, acceleration, impact etc.; and the actuated plasma decays rapidly after the strong laser pulse is stopped, during which photons with specific frequencies are radiated thereby generating characteristic spectral lines, and information of types and concentrations of elements of the object being analyzed are included in the information about frequencies and intensities of the photons. The LIBS technology has the advantages of low operating cost, fast measurement speed, high sensitivity, multi-element measurement without or with very simple pretreatment of the sample and with no radiation hazard, and thus it has great potential for development in industrial production.

However, in LIBS, as the point where laser focuses is very small, the amount of the ablated substance is very little, thus the matrix effect is significant to an inhomogeneous, anisotropic substance. Meanwhile, the variability of laser energy and the differences of physical parameter, such as the temperature of plasma, the density of electrons and the like, cause the low repeatability of the LIBS measurement. Moreover, both the influence of environmental parameters and the electrical noise from the components of the instrument per se tend to interference the LIBS. Thus, there is no guarantee to the accuracy of measuring the sample directly by the LIBS, which restricts the application of the LIBS in actual production.

In order to resolve the above problems, in the prior measurement technology, a sample is typically simply preprocessed to improve the accuracy of element measurement, for example, the sample powder is pressed to improve the reproducibility of the LIBS measurement, the sample is grinded, mixed uniformly to weaken the matrix effect etc. But the uncertainty of measurement or various influences still can not be eliminated completely and direct measurement may not achieve the accuracy required by industrial production, thus a further research for the preprocess method of sample is still needed.

SUMMARY OF THE INVENTION

In light of the above problems, one of the objects of the present invention is to provide a method and a system for improving the precision of element measurement based on laser-induced breakdown spectroscopy.

In accordance with one aspect of the present invention, there is provided a method for improving the precision of element measurement based on laser-induced breakdown spectroscopy, comprising:

Press-forming a sample to be measured with a tablet press;
making a cavity on or immediately above a surface of the press formed sample;
forming a layer of aerosol immediately above the surface of the sample to be measured with the components thereof completely identical to those of the sample to be measured;
testing the sample to be measured by using a laser-induced breakdown spectroscopic system, so as to obtain the intensities of the characteristic spectral lines of a target element in the sample to be measured;
determining the concentration of the target element in the sample to be measured according to a calibration curve of the target element in prearranged calibration samples;
wherein the calibration curve of the target element in the calibration samples is obtained by fitting a plurality of data pairs constituted by the intensities of the characteristic spectral lines of the target element in a plurality of calibration samples and the mass concentrations of the target element.

Moreover, it is a preferred scheme that the step for testing the sample to be measured by using a laser-induced breakdown spectroscopic system comprises:

emitting a laser beam by using the pulsed laser as an excitation light source;
splitting the laser beam emitted from the laser into two beams by a spectroscope;
reflecting the beams with mirrors so as to enable the angles between the incidence directions of the two laser beams split by the spectroscope and the normal direction of the surface0 of the sample to be measured to be in the range of 0°~90°;
focusing with focusing lenses the two beams of laser reflected by the mirror on or under the surface of the sample to be measured to generate plasma at the focus point;
collecting the radiation optical signal generated by the plasma with collection lens;
transmitting the radiation optical signal via optical fibers and processing the radiation optical signal so as to transform it into electrical signal with a spectrometer;
collecting the electrical signal so as to obtain the intensities of the characteristic spectral lines of the target element of the sample to be measured.

In accordance with another aspect of the present invention, there is provided a system for improving the precision of element measurement based on laser-induced breakdown spectroscopy, comprising a preprocess unit for preprocessing a sample to be measured, a laser-induced breakdown spectroscopic system and a data processing unit, wherein, the preprocess unit for preprocessing a sample to be measured comprises: a tablet press for press-forming the sample to be measured; a cavity forming unit for making a cavity on or immediately above a surface of the press formed sample to be measured; and an aerosol layer forming unit for forming a layer of aerosol immediately above the surface of the sample to be measured with the components thereof completely identical to those of the sample to be measured; the laser-induced breakdown spectroscopic system is used for testing the sample to be measured so as to obtain the intensities of the characteristic spectral lines of a target element in the sample to be measured;

the data processing unit is used for determining the concentration of the target element in the sample to be measured according to a calibration curve of the target element in a preset calibration sample, wherein the calibration curve of the target element in calibration samples is obtained by fitting a plurality of data pairs constituted by the intensities of the characteristic spectral lines of the target element in a plurality of calibration samples and the mass concentrations of the target element.

Moreover, it is a preferred structure that the laser-induced breakdown spectroscopic system comprises a pulsed laser, a spectroscope, mirrors, focusing lenses, a collection lens, optical fibers and a spectrometer, wherein, the pulsed laser is an excitation light source emitting a laser;

the spectroscope is used for splitting the laser beam emitted from the laser into two beams;

the mirrors are used for enabling the angles between the incidence directions of the two laser beams split by the spectroscope and the normal direction of the surface of the sample to be measured to be 0° to 90°;

the focusing lens is used for focusing the two beams of laser reflected by the mirror on or under the surface of the sample to be measured upon focus to generate plasma at the focus point;

the collection lens is used for collecting the radiation optical signal generated by the plasma;

the optical fibers and the spectrometer is used for transforming the radiation optical signal into an electrical signal after being processed so as to obtain the intensities of the characteristic spectral lines of the target element in the sample to be measured.

With the above method and system for improving the precision of element measurement based on laser-induced breakdown spectroscopy in accordance with the present invention, on one hand, the restriction to plasma applied by holes and cavities can be used to, with the same laser energy, increase the electron density and temperature of the plasma and improve effectively the intensities of the spectral lines and the signal to noise ratio of the plasma emission spectroscopy so as to decrease the uncertainty of the measurement method with LIBS, which is capable of decreasing the limit where microelement can be detected and improve the goodness of fit of the calibration curve. On the other hand, with the technology of impinging at an adjusted angle after light beam split, the subsequent energy of laser beam for impinging is weakened due to plasma shielding, thus more energy is applied to transform substance into plasma, and the efficiency of ablation is increased. Moreover, with the interaction mechanism between aerosol and the laser energy in accordance with the present invention, the threshold for energy required for transforming substance into plasma is lowered, and good excitation condition is provided. To sum up, with the present invention, the plasma formed by laser ablation can be more uniform and more in conformity with the condition of Local Thermodynamic Equilibrium, thereby increasing the reproducibility of the measurement and improving the precision of element measurement in laser-induced breakdown spectroscopy technology.

In order to achieve the above and other related objects, one or more aspects of the present invention include those features to be described in detail in the following and particularly pointed out in the claims. The following descriptions and accompanying drawings describe in detail certain illustrative aspects of the present invention. However, these aspects only illustrate some of the ways in which the principle of the present invention may be applied. In addition, the present invention intends to include all these aspects and their equivalents.

BRIEF DESCRIPTION OF THE DRAWINGS

Through the description below with reference to the accompanying drawings and the claims, and with a full understanding of the present invention, other purposes and effects of the present invention will be more apparent and easily understood. In the drawings:

FIG. 5(A) is a front view of the mounting position for the metal ring in the technical solution of the present invention;

FIG. 5(B) is a top view of the mounting position for the metal ring in the technical solution of the present invention;

FIG. 6(A) is a front view of the sectional view of the mold according to the technical solution of the present invention;

FIG. 6(B) is a top view of the sectional view of the mold according to the technical solution of the present invention;

REFERENCE NUMERALS IN THE DRAWINGS

210—preprocess unit for preprocessing sample to be measured;
220—laser-induced breakdown spectroscopic system;
221—pulsed laser;
222—spectroscope;
223—focusing lens;
224—sample;
225—collection lens;
226—optical fiber;
227—spectrometer;
230—data processing unit;
229—metal ring;
10—tablet press mold;
11—array of cylindrical protrusions;
12—incident laser;
13—mirror;
14—plasma Like numerals in all figures indicate similar or corresponding features or functions.

DETAILED DESCRIPTION OF THE EMBODIMENTS

Embodiments of the present invention will be described in detail with reference to the accompanying drawings.

In laser-induced breakdown spectroscopy, when a beam of strong pulsed laser being focused at a sample, the sample is instantly gasified to generate high density plasma with elevated temperature; and the plasma in excited state radiates different rays to outside, and corresponding wavelengths and intensities of the spectral lines of plasma emission spectroscopy reveal respectively the elements and their concentrations in the measured object.

Figure 1:
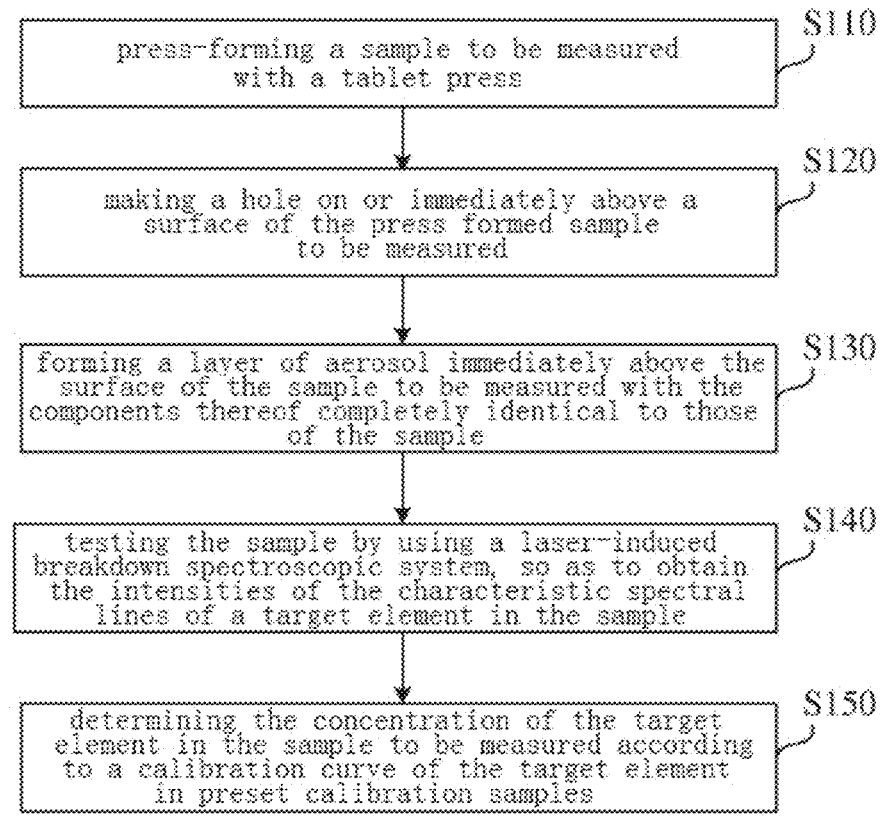
FIG. 1 is a flowchart of a method for improving the precision of element measurement based on laser-induced breakdown spectroscopy in accordance with the present invention.

A flowchart of a method for improving the precision of element measurement based on laser-induced breakdown spectroscopy in accordance with the present invention is shown in FIG. 1.

As shown in FIG. 1, the method for improving the precision of element measurement based on laser-induced breakdown spectroscopy provided by the present invention comprises the following steps:

S110: press forming a sample to be measured with a tablet press;

S120: making a cavity on or immediately above a surface of the press formed sample to be measured;

S130: forming a layer of aerosol immediately above the surface of the sample to be measured with the components thereof completely identical to those of the sample to be measured;

S140: testing the sample to be measured by using a laser-induced breakdown spectroscopic system, so as to obtain the intensities of characteristic spectral lines of a target element in the sample to be measured;

S150: determining the concentration of the target element in the sample to be measured according to a calibration curve of the target element in a preset calibration s ample.

Wherein, the calibration curve of the target element in the calibration sample is formed by fitting a plurality of data pairs composed of intensities of the characteristic spectral lines of the target element in a plurality of calibration samples and the mass concentrations of the target element.

Figure 2:
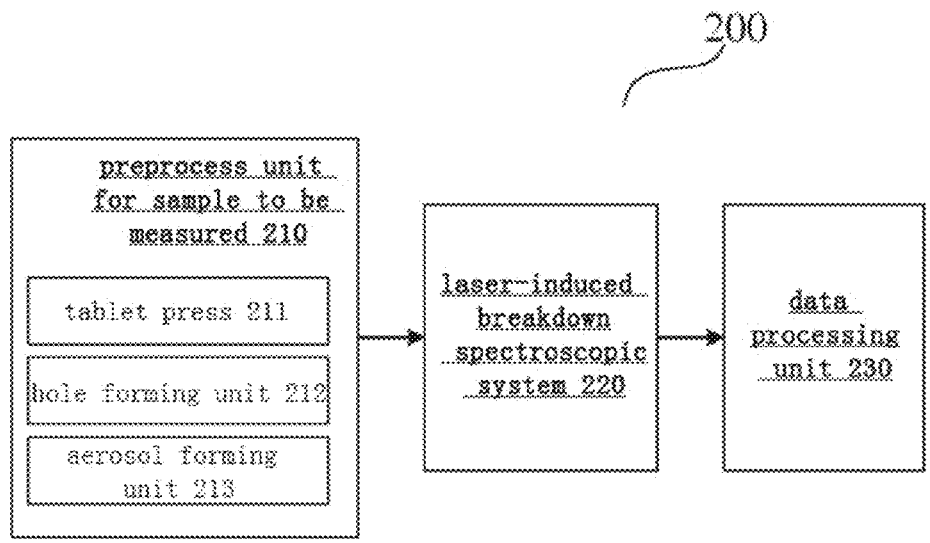
FIG. 2 is a schematic block diagram showing a system for improving the precision of element measurement based on laser-induced breakdown spectroscopy in accordance with the present invention.

FIG. 2 is a schematic block drawing of a system for improving the precision of element measurement based on laser-induced breakdown spectroscopy, which system corresponding to the flowchart of method shown in FIG. 1. Referring to FIG. 2, the system 200 for improving the precision of element measurement based on laser-induced breakdown spectroscopy comprises a preprocess unit 210 for preprocessing sample to be measured, a laser-induced breakdown spectroscopic system 220 and a data processing unit 230, wherein the preprocess unit 210 further comprises a tablet press 211, a cavity forming unit 212 and an aerosol layer forming unit 213.

The tablet press 211 is used for press-forming the sample to be measured, the cavity forming unit 212 is used for making a cavity on or immediately above a surface of the press-formed sample, and the aerosol layer forming unit 213 is used for forming a layer of aerosol immediately above the surface of the sample to be measured with the components thereof completely identical to those of the sample to be measured. The laser-induced breakdown spectroscopic system 220 is used for testing the sample to be measured so as to obtain the intensities of the characteristic spectral lines of a target element in the sample to be measured. The data processing unit 230 is used for determining the concentration of the target element in the sample to be measured according to a calibration curve of the target element in a preset calibration sample.

The steps for testing the sample to be measured by using the above laser-induced breakdown spectroscopic system 220 comprises:

emitting a laser beam by using the pulsed laser as a light source;

splitting the laser beam emitted from the laser into two beams by a spectroscope;

reflecting the two laser beams using mirrors so as to enable the angles between the incidence directions of the two laser beams split by the spectroscope and the normal direction of the surface of the sample to be measured to be in the range of 0°~90°;

focusing the two beams of laser reflected by the mirrors on or under the surface of the sample to be measured by focusing lens to generate plasma at the focus point;

collecting signals of rays radiated by the plasma with a collection lens;

transforming the signals of rays radiated into electrical signals after being processed using a spectrometer and via optical fibers;

collecting the electrical signals so as to obtain the intensities of the characteristic spectral lines of the target element of the sample to be measured.

Figure 3A:
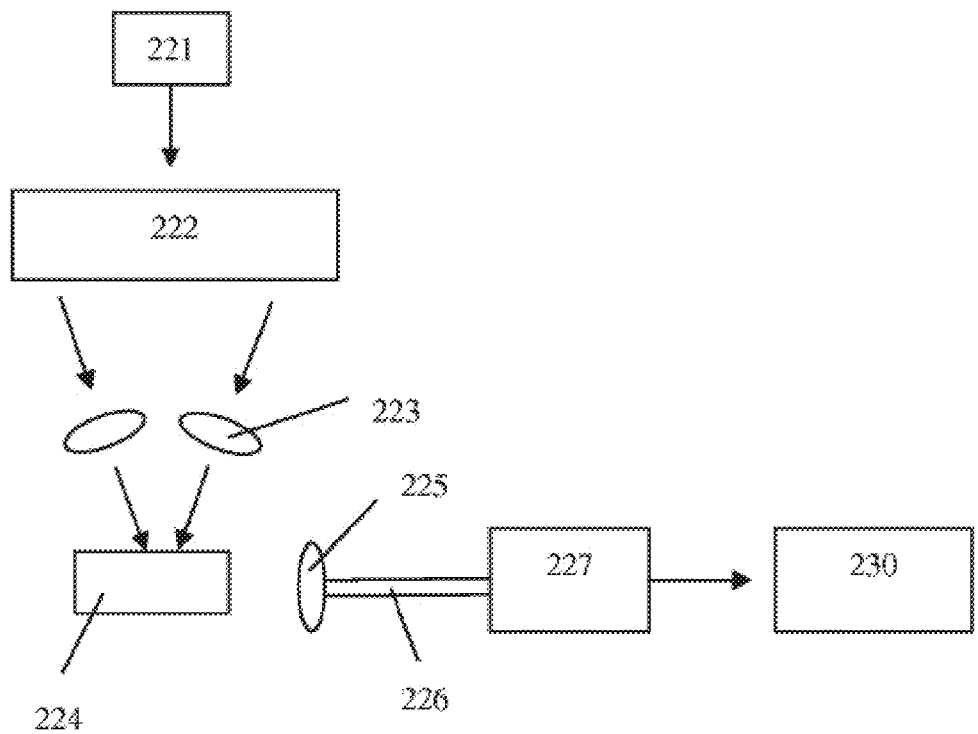
FIG. 3(A) is a block diagram showing the structure of a laser-induced breakdown spectroscopic system in accordance with the present invention.

FIG. 3(A) is a structure diagram of a laser-induced breakdown spectroscopic system in accordance with the present invention. As shown in FIG. 3(A), the laser-induced breakdown spectroscopic system 220 comprises a pulsed laser 221, a spectroscope 222, mirrors (not shown), focusing lenses 223, a collection lens 225, optical fibers 226 and a spectrometer 227.

As an example, particularly, when the concentration of the target element in the sample is required to be measured, the element to be measured in the sample is determined as a target element, and a set of samples, in which the mass concentrations of the target element are known, is determined as calibration samples.

Figure 3B:
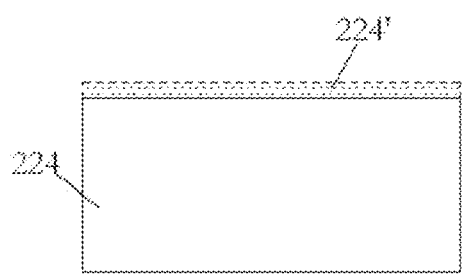
FIG. 3(B) is a schematic view showing a sample with a layer of aerosol on the top surface of the sample.

During the stage of preprocessing the sample, firstly, the calibration sample or the sample 224 to be measured is press-formed by a tablet press 211, in an embodiment of the present invention, the sample is pressed into a shape of a round pie with a smooth surface; and then a hole or cavity is formed on or immediately above a surface of the calibration sample by the cavity forming unit 212; finally, a layer of aerosol is formed by the aerosol layer forming unit 213 immediately above the surface of the calibration sample with the components thereof completely identical to those of the calibration sample. FIG. 3(B) schematically shows a sample 224 with a layer of aerosol 224' on the top surface of the sample.

The method of forming a hole or cavity on a surface of the calibration sample or the sample to be measured by the cavity forming unit 212 comprises the following several types of methods:

the first method: the calibration sample or the sample to be measured, which is pressed to be a round pie, is fixed on a base driven by a stepper motor, and is freely movable in a two dimension plane, and then the round pie is impinged by a laser beam so as to form one or more holes with a relatively stable volume;

the second method: the calibration sample or the sample to be measured, which is pressed to be a round pie, is fixed on a base driven by a stepper motor, and is freely movable in a two dimension plane, and then the surface of the round pie is covered by a sheet metal with round through holes arranged in an array, and holes in correspondence with the above round through holes are formed immediately above the surface of the round pie.

Figure 4:
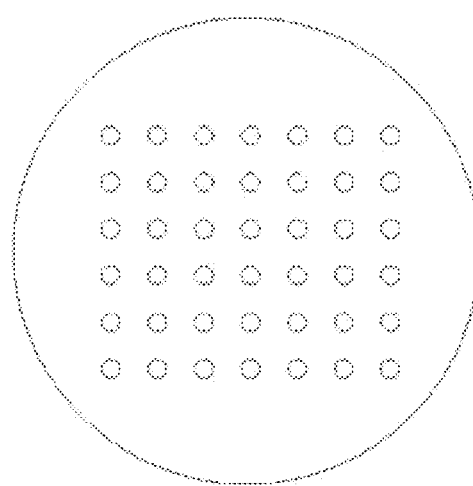
FIG. 4 is a schematic diagram of a metal sheet covering the surface of the sample in the technical solution of the present invention.

FIG. 4 is a diagram showing an embodiment of the metal sheet covering the surface of the sample according to the present invention. As shown in FIG. 4, the surface of the round pie is covered by the sheet metal with round through holes arranged in an array, wherein the sheet metal has a thickness of 1-3 mm and the diameters of the round holes are 1-3 mm, thus cavities corresponding to the round through holes one by one are formed immediately above the surface of the round pie.

The third method: the calibration sample or the sample to be measured, which is pressed to be a round pie, is fixed on a base driven by a stepper motor, and is freely movable in a two dimension plane, and then a metal ring, whose internal diameter ranges from 1 mm to 3 mm, is fixed on the container of the focusing lens so as to align the center of the metal ring and the center of the focusing lens on the same straight line, the bottom surface of the metal ring is firmly attached to the round pie, and a cavity is formed immediately above the surface of the round pie where the metal ring is attached.

FIG. 5(A) and FIG. 5(B) are a front view and a top view of the mounting position of the metal ring in accordance with the embodiment of the present invention, respectively. As shown in FIG. 5(A) and FIG. 5(B), a metal ring 229, whose internal diameter ranges from 1 mm to 3 mm, is fixed on the container inside of which the the focusing lens 223 is fixed so as to enable the center of the metal ring 229 and the center of the focusing lens 223 on the same straight line, the bottom surface of the metal ring is firmly attached to the round pie, and thus a cavity is formed immediately above the surface of the round pie where the metal ring is attached.

The fourth method: a tablet press mold with a array of cylindrical protrusions on the surface thereof is fabricated, the calibration sample or the sample to be measured is pressed as a round pie by the tablet press mold, and the array of cylindrical protrusions on the tablet press mold form holes on the surfaces of the round pies during pressing the calibration sample or the sample to be measured into round pies.

FIG. 6(A) and FIG. 6(B) are a front cross-sectional view and a top cross-sectional view of the mold according to an embodiment of the present invention, respectively. In the embodiment as shown in FIG. 6(A) and FIG. 6(B), the tablet press mold 10 is provided at the surface with an array of cylindrical protrusions 11 whose diameters and heights both ranges from 1 mm to 3 mm, when the calibration sample or the sample to be measured is pressed as a round pie by the tablet press mold 10, holes whose diameter and depth both range from 1 mm to 3 mm are formed on the surface of the round pie by the effect of the array of cylindrical protrusions 11.

Also, according to an embodiment of the present invention, there are following two methods for forming aerosol over the surface of the calibration sample or the sample to be measured:

the first method: with respect to any kind of the calibration sample or the sample to be measured, firstly, the sample is pressed by the tablet press 211, another part of the same kind of sample is grinded into granules of submicron order in size, and is mingled uniformly with protective gas so as to form aerosol, and then the aerosol is sprayed via a nozzle above the surface of the pressed calibration sample or the sample to be measured. The protective gas is air, nitrogen gas or inert gas.

The second method: with respect to any kind of the calibration sample or the sample to be measured, the press formed sample is disposed in a container with a gas inlet and a gas outlet, another part of the same kind of sample is grinded into granules of submicron order in size, and dispersed uniformly on the surface of the pressed calibration sample or the sample to be measured. The flow of the protective gas in the container is controlled by controlling the gas inlet and the gas outlet of the container such that relatively stable aerosol is formed inside the container, thereby covering the surface of the sample under a stable ambient.

After holes and an aerosol layer are formed on the surface of the sample, the laser-induced breakdown spectroscopic system 220 shown in FIG. 3(A) can be used for testing the sample subjected to preprocess: the pulsed laser 221 is used as a excitation light source to emit a laser beam, and the laser beam emitted from the laser is firstly split into two beams by the spectroscope 222, the angles between the incidence directions of the two laser beams and the normal direction of the surface of the sample is made to be 0°~90° after being reflected by the mirrors; the two beams of laser are focused on or under the surface of the calibration sample or the sample to be measured 224 by focusing lenses 223 so as to generate plasma at the focus point; the optical signal radiated by the plasma is collected by the collection lens 225, and is transferred through the optical fiber 226 and transformed into an electrical signal after being processed by the spectrometer 227, and then collected and processed by the data processing unit 230 so as to obtain the characteristic spectrum plot of the calibration sample or the sample to be measured, thereby obtaining the intensities $I_c$ of the characteristic spectral lines of the target element from the characteristic spectrum plot.

The intensity $I_c$ of the characteristic spectral line of a target element in the calibration sample and the mass concentration (C) of the target element make a data pair $(C, I_c)$, and a plurality of data pairs corresponding to a plurality of calibration samples are obtained, and then a calibration curve is obtained by fitting the data paires with an univariate calibration method, wherein the horizontal axis of the calibration curve is the mass concentration C of the element, and the vertical axis is $I_c$.

4) When testing a sample where mass concentration of a target element is unknown, firstly, the sample is precessed according to the above method so as to obtain the intensity $I_c'$ of the characteristic spectral line of the target element in the sample, which is then substituted into the calibration curve determined according to the test of the calibration sample, thereby determining the intensity C' of the target element in the sample.

Now, the method and system for improving the accuracy of element measurement based on the Laser-induced breakdown spectroscopy in accordance with the present invention will be described by means of an example, where the carbon element in coal being measured by LIBS.

1) Firstly, ten standard coal samples where mass concentration of each element is known is used for analysis, wherein the mass concentrations and the volatile contents of the main elements of each coal sample are shown in Table 1; and the samples are processed by the method for fabricating four holes or cavities and two methods for forming aerosol according to the application.

TABLE 1

Components of standard coal sample

| No. | Carbon (%) | Hydrogen (%) | Nitrogen (%) | Volatile (%) |
| --- | --- | --- | --- | --- |
| GBW11101n | 52.61 | 3.45 | 1.00 | 23.23 |
| GBW11102k | 53.42 | 3.50 | 0.97 | 25.58 |
| GBW11107L | 59.91 | 3.90 | 1.11 | 28.90 |
| GBW11108h | 67.77 | 4.25 | 1.20 | 34.46 |
| GBW11109f | 55.67 | 3.22 | 1.02 | 19.11 |
| GBW11110g | 61.49 | 2.98 | 0.97 | 18.25 |
| GBW11111d | 70.45 | 3.40 | 1.15 | 14.41 |
| ZBM096 | 81.45 | 3.52 | 1.34 | 11.00 |
| ZBM097 | 81.54 | 3.70 | 1.16 | 12.43 |
| ZBM098 | 78.98 | 4.95 | 1.38 | 31.92 |
| ZBM099 | 79.90 | 3.80 | 1.10 | 15.30 |

Figure 3C:
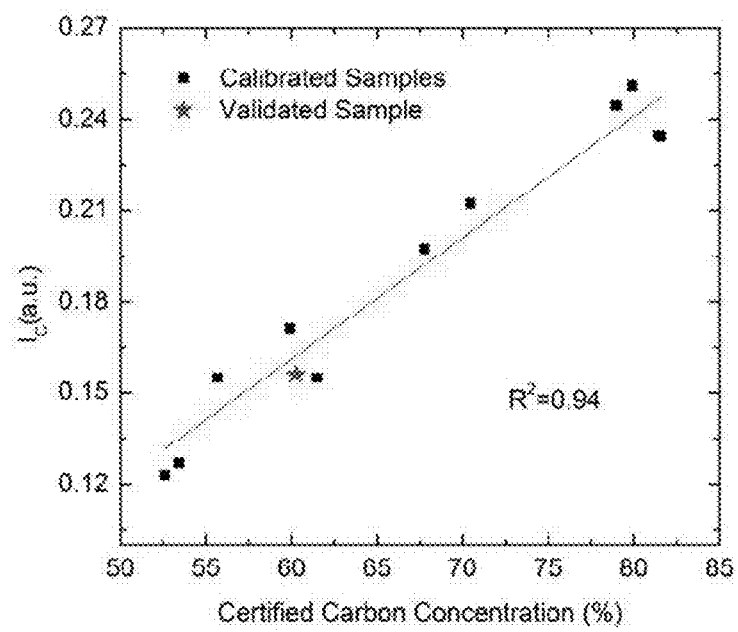
FIG. 3(C) shows, as an example, a calibration curve of element C in coal.

As an example, FIG. 3(C) shows a calibration curve of element C in coal.

2) The laser-induced breakdown spectroscopic system 220 as shown in FIG. 3(A) is used for testing the sample; the pulsed laser 221 is used as a excitation light source to emit a laser beam, which laser beam is firstly split into two beams by the spectroscope 222, the angles between the incidence directions of the two laser beams and the normal direction of the surface of the sample is made to be 0°~90° after reflected by the mirrors; the two beams of laser are focused on or under the surface of the calibration sample 224 by focusing lenses 223 to generate plasma at the focus point; the optical signal radiated by the plasma is collected by the collection lens 225, and is transmitted through the optical fiber 226 and transformed into an electrical signal through the spectrometer 227, and is collected and processed by the data processing unit 230 so as to obtain a set of standard spectral lines of coal sample of which mass concentration of carbon concentration is already known, and further obtain the intensities $I_c$ of the characteristic spectral lines of the laser-induced breakdown spectrum of each element in the coal sample.

3) The intensities $I_c$ of the characteristic spectral lines of the carbon element in the calibration sample and the mass concentrations (C) of the carbon element make a data pair $(C, I_c)$, and a plurality of data pairs are obtained for a plurality of calibration samples, and then a calibration curve is obtained by fitting the dada pairs, wherein the horizontal axis of the calibration curve is the mass concentration of carbon element, and the vertical axis is $I_c$; the goodness of fit of the calibration curve obtained by least square method is 0.94.

4) When detecting the mass concentration of carbon element in the coal sample, firstly, the sample is processed according to step (1) and step (2) so as to obtain the intensity of the characteristic spectral line of LIBS spectrum of carbon element, and the concentration of carbon element in the coal sample is determined by using the calibration curve obtained in step (3).

In order to verify the accuracy of the method, when the coal sample, of which the mass concentration of each element is 60.26% of carbon, 2.75% of hydrogen, 1.06% of nitrogen, is used as the sample to be measured, the mass concentration of carbon element of the coal sample obtained by through the said measurement is 59.26%, and the relative error of measurement is 1.66%. As can be seen from the above measurement data, the method of present invention has a higher accuracy and meets the requirement of manufacture.

Wherein, the space restriction to plasma applied by the holes or cavities is one of the key points of the present invention.

In low pressure ambient, the plasma is divided into two parts, the first part is the plasma with high temperature and high pressure at the beginning which is close to the surface of sample and physically small, short in lifetime, radiates very strong continue background radiation, and which is referred as primary plasma, which is actuated by laser; the second part is secondary plasma which surrounds the primary plasma, radiates discrete spectral lines and very tiny background radiation, and is actuated by shock wave; generally, the secondary plasma is generated only when laser is strong enough. So to speak, the generation of the secondary laser is the basis of laser-induced spectroscopy in element analysis, and the increase in electron density and temperature of the secondary plasma can improve the intensity of spectral line of the measured spectrum and its signal to noise ratio.

When there are holes or cavities, laser impinging on the bottoms of the holes or cavities generates primary plasma, and shock wave tends to be generated due to space restriction during the expansion of the primary plasma, the kinetic energy of atoms is transformed into thermal energy due to adiabatic compression effect of shock wave; the thus generated plasma has higher electron density than that of the plasma generated due to laser directly impinging on the surface; afterwards, the plasma with high electron density has stronger absorption of the energy of laser due to inverse bremsstrahlung, thereby further increasing the electron density in the plasma. The increase in electron density relates to the dimension of the hole or cavity. The larger depth to diameter ratio of the hole or cavity, the higher electron density. However, the temperature of plasma will decrease due to heat conduction of the walls of the hole or cavity, thereby affecting the measured intensities of the spectral lines, thus proper depth to diameter ratio is required to obtain a reasonably good emission spectrum. To sum up, with the same level of laser energy, the emission spectrum of the plasma, when there are holes or cavities, has higher intensities of the spectral lines and a greater signal to noise ratio, which contributes to decrease in the detection limit of microelement in the sample.

The uncertainty of measurement method with laser-induced breakdown spectrum mainly comes from the following aspects: inhomogeneity of temperature or electron density, total particle population in the plasma and the variation of the shape of the plasma. The variation of the shape of the plasma is decreased and the ablation quality is more stable due to space restriction applied by the cavities, so that the uncertainty can be decreased, thereby enabling the calibration curve have better goodness of fit.

The effect of the aerosol is another key point of the present invention. In aerosol ambient, particles are able to evaporate sufficiently and reduce the influence of matrix effect; furthermore, the interaction between particles and plasma dominates the process of the evolution of plasma, however, a laser beam rarely interacts with the particles of the sample, under pure gas ambient, the main components in plasma are gas. Therefore, preparation of aerosol ambient with components thereof identical to that of the sample contributes to increase in the population of particles of the sample in the plasma, enhancing the LIBS signal of the element to be measured, thereby decreasing the Relative Standard Deviation (RSD) of the measurement and improving the reproducibility and accuracy of the experiment.

The optical spectroscopy has advantages as follows, with the same level of laser energy, adjusting the incident angle of a laser beam and weakening the effect of plasma shielding will function as improving the ablation quality of the sample. It is generally proposed that, during the diffusion process of plasma, the interaction between plasma and the particles is the strongest and the generated electron density is higher in the direction perpendicular to the surface of the sample, furthermore, the energy of plasma in the direction perpendicular to the surface of the sample is more concentrated and the electron density is further increased in connection with the space restriction applied by the holes or cavities of the present invention. In order to weaken the effect of plasma shielding, optical spectroscopy is applied to the present invention to split the incident laser into two beams so as to radiate to the surface of the sample at a certain angle to the normal direction of the surface of the sample. Therefore, with the same laser energy, there can be higher energy interacting with the surface of the sample so as to improve the utilization rate of energy and improve the level of ablation of the sample, thereby lowering the uncertainty of measurement by laser-induced breakdown spectroscopy technology.

Figure 7:
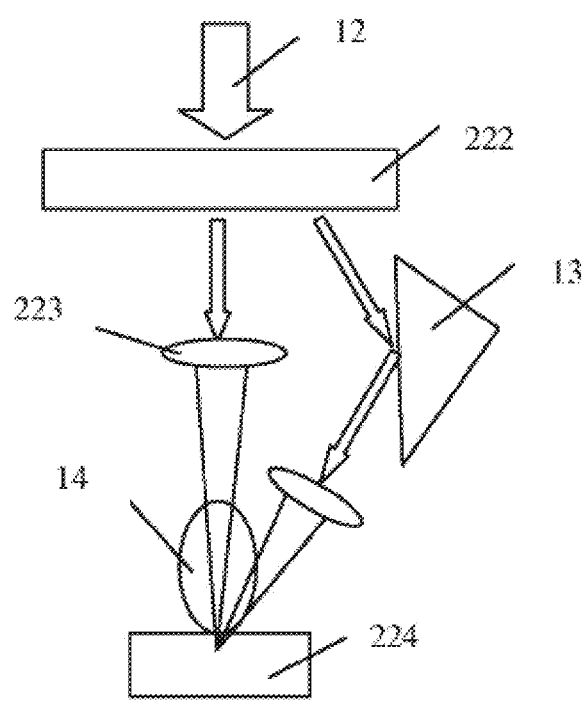
FIG. 7 is a schematic diagram of the optical spectroscopy according to the technical solution of the present invention.

FIG. 7 is a schematic diagram of the optical spectroscopy in the technical solution according to the present invention. As shown in FIG. 7, an incident laser beam 12 emitted by a pulsed laser is dispersed by a spectroscope 222, and then the dispersed laser beams are irradiated to the surface of the sample 224 under the action of a mirror 13 and a focusing lens 223, at this time, in the direction perpendicular to the surface of the sample, the interaction between plasma 14 and the particles is the strongest and the density of generated electron is higher, and the energy for ablation of the sample is more concentrated.

To sum up the above analysis, the sample is preprocessed effectively prior to detection and the incident angle of a laser is adjusted in the present invention such that the plasma generated by laser ablation is more uniform and more in conformity with the condition of Local Thermodynamic Equilibrium (LTE), thereby increasing the reproducibility of the measurement and improving the precision of element measurement in laser-induced breakdown spectroscopy technology. The method provided by the present invention has the advantages of high detection sensitivity, lower production cost, and capable of analyzing multiple elements at the same time.

So far, the method and system according to the present application for improving precision of element detection on the basis of laser-induced breakdown spectroscopy technology have been described by way of examples with reference to the Drawings. Yet, persons skilled in the art will appreciate that, various of changes and modifications will be made with respect to the above-described example without departure of the spirit of the present invention. The protection scope of the invention therefore will be defined by the following claims.

What is claimed is:

1. A method for improving the precision of element measurement based on laser-induced breakdown spectroscopy, comprising:
   press-forming a sample to be measured with a tablet press;
   making a cavity on a surface of the sample;
   forming a layer of aerosol immediately above the surface of the sample to be measured with the components of the layer of aerosol completely identical to those of the sample;
   testing the sample by using a laser-induced breakdown spectroscopic system, so as to obtain the intensities of the characteristic spectral lines of a target element in the sample;
   determining the concentration of the target element in the sample to be measured according to a calibration curve of the target element in a set of prepared calibration samples;
   wherein the calibration curve of the target element in the calibration samples is obtained by fitting a plurality of data pairs constituted by the intensities of the characteristic spectral lines of the target element in a plurality of calibration samples and the mass concentrations of the target element in the samples.

2. The method for improving the precision of element measurement based on laser-induced breakdown spectroscopy of claim 1, wherein the step for testing the sample by using a laser-induced breakdown spectroscopic system comprises:
   emitting a laser beam by using the pulsed laser as an excitation light source;
   splitting the laser beam emitted from the laser into two beams by a spectroscope;
   reflecting the beams with minors so as to arrange the angles between the incidence directions of the two laser beams split by the spectroscope and the normal direction of the surface of the sample in the range of 0°~90°;
   focusing the two beams of laser reflected by the minors on or under the surface of the sample to be measured using focusing lenses so as to generate plasma at the focus point;
   collecting the radiation optical signal generated by the plasma with a collection lens;
   transmitting the radiation optical signal via a optical fiber and processing it with a spectrometer to transforming the radiation optical signal into an electrical signal;
   collecting the electrical signal so as to obtain the intensities of the characteristic spectral lines of the target element of the sample to be measured.

3. The method for improving the precision of element measurement based on laser-induced breakdown spectroscopy of claim 1, wherein the step for making a cavity on a surface of the sample comprises:
   fabricating a tablet press mold with an array of cylindrical protrusions with diameter range of 1-3 mm, height range of 1-3 mm on the surface thereof, and pressing the sample to be measured by the tablet press mold, and leaving holes on the surface of the sample during the pressing process by the array of cylindrical protrusions on the tablet press mold.

4. The method for improving the precision of element measurement based on laser-induced breakdown spectroscopy of claim 1, wherein, the step for forming a layer of aerosol immediately above the surface of the sample to be measured with the components thereof completely identical to those of the sample to be measured comprises:
   grinding a part of the sample into granules of submicron order in size which are mingled uniformly with protective gas so as to form aerosol;
   then spraying the aerosol above the surface of the press-formed the sample to be measured with a spray nozzle; or, dispersing uniformly the aerosol on the surface of press-formed sample by using a container having a gas inlet and a gas outlet, wherein, the flow of gas in the container is controlled by controlling the gas inlet and the gas outlet of the container so as to forming stable aerosol inside the container.

5. The method for improving the precision of element measurement based on laser-induced breakdown spectroscopy of claim 4, wherein the protective gas is air, nitrogen gas or inert gas.

6. The method for improving the precision of element measurement based on laser-induced breakdown spectroscopy of claim 1 any one of claims 1 to 5, wherein the step for obtaining the calibration curve of the target element in calibration samples comprises:
   press-forming a calibration sample with a tablet press;
   making a cavity on a surface of the press-formed calibration sample;
   forming a layer of aerosol immediately above the surface of the calibration sample with the components thereof completely identical to those of the calibration sample;
   testing the calibration sample by using a laser-induced breakdown spectroscopic system, so as to obtain the intensities of the characteristic spectral lines of a target element in the calibration sample;
   making data pairs by using the intensities of the characteristic spectral lines of the target element in calibration samples and the mass concentrations of the target element in the calibration samples;
   obtaining the calibration curve of the target element in the calibration samples by fitting a predetermined number of the data pairs of the calibration element according to the univariate calibration method.

7. A system for improving the precision of element measurement based on laser-induced breakdown spectroscopy, comprising a preprocess unit for preprocessing a sample to be measured, a laser-induced breakdown spectroscopic system and a data processing unit, wherein,
  the preprocess unit for preprocessing a sample to be measured comprises:
    a tablet press for pressing the sample to be measured;
    a cavity forming unit for making a cavity on a surface of the sample; and,
    an aerosol layer forming unit configured to form a layer of aerosol immediately above the surface of the sample to be measured with the components thereof completely identical to those of the sample to be measured;
  the laser-induced breakdown spectroscopic system configured to test the sample to be measured so as to obtain the intensities of the characteristic spectral lines of a target element in the sample;
  the data processing unit configured to determine the concentration of the target element in the sample to be measured according to a calibration curve of the target element in a pre-prepared set of calibration samples,
  wherein the calibration curve of the target element in the calibration sample is obtained by fitting a plurality of data pairs constituted by the intensities of the characteristic spectral lines of the target element in a plurality of calibration samples and mass concentration values of the target element in the calibration samples.

8. The system for improving the precision of element measurement based on laser-induced breakdown spectroscopy of claim 7, the laser-induced breakdown spectroscopic system comprises a pulsed laser, a spectroscope, mirrors, focusing lenses, a collection lens, optical fibers and a spectrometer, wherein,
  the pulsed laser is an excitation light source emitting a laser beam;
  the spectroscope is used for splitting the laser beam emitted from the laser into two beams;
  the minors reflect the two laser beams split by the spectroscope so as to rendering the angles between the incidence directions of the two laser beams and the normal direction of the surface of the sample to be measured to be in the range of 0° to 90°;
  the focusing lenses focus the two beams of laser reflected by the minor on or under the surface of the sample to be measured to generate plasma at the focus point;
  the collection lens is used for collecting the radiation optical signal generated by the plasma;
  the optical fibers transmit the radiation optical signal and the spectrometer processes the radiation optical signal and transforms the radiation optical signal into an electrical signal after so as to obtain the intensities of the characteristic spectral lines of the target element in the sample to be measured.

\* \* \* \* \*